United States Patent
Rosenberg

(10) Patent No.: US 9,060,950 B2
(45) Date of Patent: Jun. 23, 2015

(54) EMETIC EMBEDDED CAPSULE

(75) Inventor: Paul Rosenberg, Saddle River, NJ (US)

(73) Assignee: Paul H. Rosenberg, Proximate Concepts, LLC., Fort Lee, NJ (US)

( * ) Notice: Subject to any disclaimer, the term of this patent is extended or adjusted under 35 U.S.C. 154(b) by 1956 days.

(21) Appl. No.: 12/001,877

(22) Filed: Dec. 13, 2007

(65) Prior Publication Data

US 2008/0102113 A1   May 1, 2008

Related U.S. Application Data

(63) Continuation of application No. PCT/US2006/022939, filed on Jun. 13, 2006.

(60) Provisional application No. 60/690,023, filed on Jun. 13, 2005.

(51) Int. Cl.
*A61K 9/48* (2006.01)

(52) U.S. Cl.
CPC .............. *A61K 9/4833* (2013.01); *A61K 9/4816* (2013.01); *A61K 9/4866* (2013.01)

(58) Field of Classification Search
CPC ...... A61K 9/48; A61K 9/4808; A61K 9/4816; A61K 9/4841; A61K 9/485; A61K 9/5057
USPC ........................................................ 424/458
See application file for complete search history.

(56) References Cited

U.S. PATENT DOCUMENTS

| | | | | |
|---|---|---|---|---|
| 3,702,653 | A | * 11/1972 | Mottin et al. | ................. 206/534 |
| 4,175,119 | A | 11/1979 | Porter | |
| 4,269,820 | A | 5/1981 | Davies et al. | |
| 4,457,907 | A | 7/1984 | Porter | |
| 4,529,583 | A | 7/1985 | Porter | |
| 5,641,512 | A | * 6/1997 | Cimiluca | ...................... 424/455 |
| 5,756,123 | A | 5/1998 | Yamamoto et al. | |
| 6,214,376 | B1 | 4/2001 | Gennadios | |
| 6,316,025 | B1 | 11/2001 | Grattan | |
| 2003/0044458 | A1 | * 3/2003 | Wright et al. | ................. 424/458 |
| 2003/0124061 | A1 | 7/2003 | Roberts | |
| 2003/0125347 | A1 | 7/2003 | Anderson et al. | |
| 2003/0170181 | A1 | 9/2003 | Midha | |
| 2006/0110327 | A1 | 5/2006 | Emigh et al. | |
| 2006/0165602 | A1 | 7/2006 | Galer et al. | |

FOREIGN PATENT DOCUMENTS

| | | |
|---|---|---|
| GB | 1428361 | 3/1976 |
| WO | WO 02/094172 | 11/2002 |
| WO | WO 02094172 A2 * | 11/2002 |
| WO | WO 03/013538 | 2/2003 |

\* cited by examiner

*Primary Examiner* — Michael G Hartley
*Assistant Examiner* — Micah-Paul Young

(57) ABSTRACT

This invention provides capsules containing an emetic, which capsules can encapsulate a drug, wherein the amount of emetic and the amount of drug is such that the number of capsules needed to be ingested to cause emesis is fewer than the number of capsules needed to be ingested to cause overdose of the drug, so that if a person takes an overdose of the emetic encapsulated drug, he or she will vomit before the drug is absorbed by the body.

22 Claims, 1 Drawing Sheet

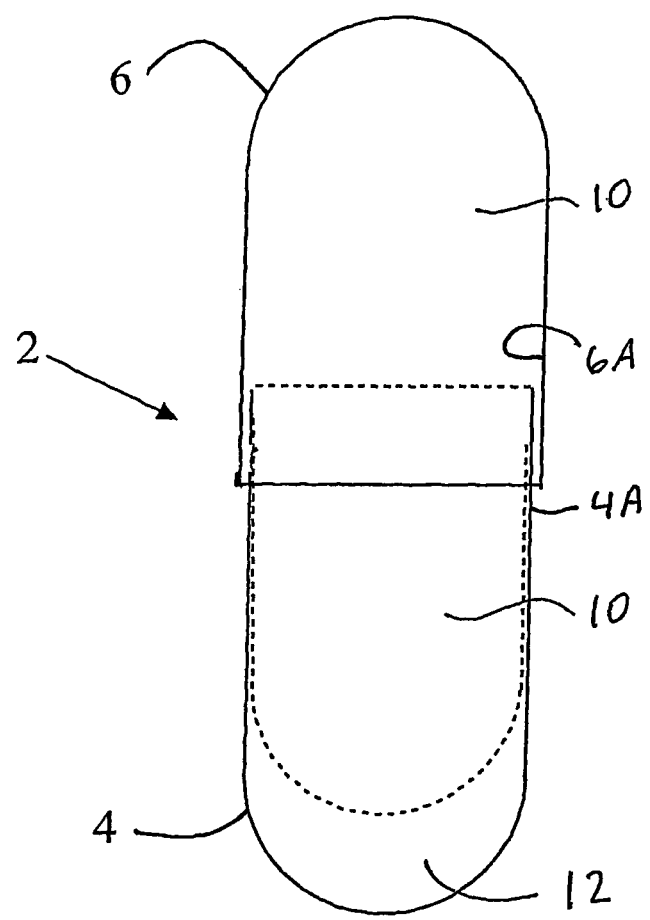

EMETIC EMBEDDED CAPSULE

CROSS-REFERENCE TO RELATED APPLICATIONS

This application is a continuation of International Application No. PCT/US2006/022939, which claims priority to U.S. Provisional Application 60/690,023 filed Jun. 13, 2005, the contents of each of which are herein incorporated by reference.

BACKGROUND OF THE INVENTION

All drugs have the potential to be misused, whether the drugs are legally prescribed by a physician, or purchased over-the-counter at a store. When ingested in excessive quantities, drugs normally considered safe can cause death or serious bodily damage.

Accidental and purposeful overdose or death by over consumption of drugs is a serious problem. People ingest drugs to attempt suicide and are often successful. People who suffer from depression and who have suicidal thoughts are also at high risk for drug overdose. Drug addicts ingest and consume quantities of drugs to elicit mind and mood altering effects, potentially causing serious injury to their bodies. Children are able to open containers containing any variety of drugs and innocently ingest or consume the drugs without knowledge of the consequences, even with the advent of tamper proof containers.

Accidental drug overdose may be the result of misuse of prescription medicines or commonly used medications like pain relievers and cold remedies. Between 1970 and 2000, some 131,000 people died by accidental drug overdose. While a small percentage (3 percent) of the deaths were from adverse effects of the right drug taken at the right dose, 97 percent of the deaths resulted from medication errors including ingesting a wrong dose, or accidental overdose of a drug. According to the National Institute on Drug Abuse, in 1992, almost 6,000 deaths were the result of accidental overdose of psychoactive and other drugs. Patients treated with antidepressant medications, i.e., GSK's WELLBUTRIN® and PAXIL® (paroxetine), Eli Lilly's PROZAC® (fluoxetine), Pfizer's ZOLOFT® (sertraline), Solvay's LUVOX® (fluvoxamine), Forest Laboratories'CELEXA® (citalopram) and LEXAPRO® (escitalopram), Wyeth's EFFEXOR® (venlafaxine), Bristol-Myers Squibb's SERZONE® (nefazodone) and Organon's REMERON® (mirtazapine), may have an increased risk of suicidal thoughts and behaviour.

Accordingly, there is a great need for dosage forms to prevent accidental or intentional overdose of drugs.

It is known in the art that emetics may be incorporated into drug compositions, or admixed with a drug. Following ingestion, the drug and emetic would be simultaneously released in the stomach. However, this requires development of formulations and compositions which are compatible and otherwise suitable for use with both the drug and the emetic, and further requires that the drug and the emetic be chemically compatible with each other. Additionally, combining an emetic and drug in a single composition would cause the emetic and drug to be released simultaneously following ingestion, thus there is a danger that a dangerous or toxic amount of drug can be absorbed into the body prior to emesis of the drug.

U.S. Pat. Nos. 4,175,119 and 4,529,583, herein incorporated by reference, disclose a medicinal composition whereby a tablet or capsule is coated with an emetic to prevent accidental or purposeful drug overdose. However, this requires the use of coating machines which health care professionals may not have access to.

Thus a need exists for an emetic dosage form which may be employed for the delivery of a wide range of drugs and which permits flexibility in dosing of the drug and emetic.

Additionally, a need exists for an emetic dosage form which may be employed for the delivery of a wide range of drugs and which permits customized dosing of the drug and emetic for individual patients.

Additionally, a need exists for a method for manufacturing and administering an emetic dosage form allowing health care professionals to tailor various drugs in variable amounts for individuals that may ingest an overdose of a drug.

Additionally, a need exists for a method to customize an emetic dosage to induce emesis before drugs are absorbed in a human, potentially causing an overdose.

SUMMARY OF THE INVENTION

The present invention provides capsules containing an emetic, which capsules can encapsulate a drug, wherein the amount of emetic and the amount of drug is such that the number of capsules needed to be ingested to cause emesis is fewer than the number of capsules needed to be ingested to cause overdose of the drug, so that if a person takes an overdose of the emetic encapsulated drug, he or she will vomit before an amount of drug is absorbed by the body which may cause an overdose.

The present invention is thus directed to a capsule comprising an emetic.

In one embodiment of the present invention, an emetic embedded piece is formed from an admixture comprising a matrix, a plasticizer, and an emetic.

In another embodiment of the present invention, an emetic embedded piece is formed from an admixture comprising a matrix, a plasticizer, and an emetic, the piece also having a sub-compartment to hold the same or a different emetic in the admixture.

In another embodiment of the present invention, an emetic embedded capsule is formed with at least one emetic embedded piece, and a second capsule piece. An emetic embedded capsule can also be formed by encapsulating a drug within a sub-chamber of an emetic embedded piece, and an emetic is encapsulated within the main chamber of the capsule.

In still another embodiment of the present invention, an emetic embedded capsule is suitable for use in a method of inducing emesis in the body of a being to preclude injury or death from accidental or intentional overdose of a drug, which is normally of the type which if ingested properly (i.e., by prescription or instructions) is safe, but if ingested in excessive quantities is potentially toxic, potentially lethal, toxic, or lethal.

In still another embodiment of the present invention, a drug is encapsulated within an emetic embedded capsule to form an emetic encapsulated drug.

In still another embodiment, a central and/or gastric emetic is used as an emetic.

In still another embodiment, an emetic having both central and gastric effect is used in an emetic embedded capsule or an emetic embedded piece.

In still another embodiment of the present invention, an emetic embedded capsule or piece can contain different amount of emetics having a particular emetic dose, so that an appropriate emetic embedded capsule or piece can be selected for a particular drug, for a particular drug dosage, and/or for a particular patient.

In still another embodiment, different color emetic embedded capsules or pieces may signify different amounts of emetics contained within an emetic embedded capsule or piece.

In still another embodiment of the present invention, emetic embedded capsules or pieces may contain different types of emetics or mixtures of emetics, so that an appropriate emetic embedded capsule or piece can be selected for a particular drug, for a particular drug dosage, or for a particular patient.

In still another embodiment, different color emetic embedded capsules or pieces may signify different types of emetic chemicals present in an emetic embedded capsule or piece.

In still another embodiment of the present invention, a laxative may be substituted for the emetic.

In still another embodiment of the present invention, the capsules may contain fragrances and flavors.

In still another embodiment of the present invention, the capsule contains an inert material so that when the capsule is ingested in normal quantities, the emetic can be passed through the gastrointestinal tract with aid of the inert material, and the emetic is not substantially absorbed into the body. However, when the capsule is ingested in quantities to induce emesis, then the inert material will not prevent emesis.

Other objects of the present invention will become apparent from a review of the present specification.

DESCRIPTION OF THE DRAWINGS

FIG. 1 is an emetic embedded capsule in accordance with the present invention.

DETAILED DESCRIPTION OF THE INVENTION

As shown in FIG. 1, capsules 2 for dosing of drugs are well known in the art. A capsule, i.e., a hard gelatin or hard gel capsule, generally comes in two pieces, a male piece 4 and a female piece 6, whereby both pieces cooperatively operate to engage another, generally the male piece 4 fitting into the female piece 6. Generally, the two pieces each have an outer circumference, a thickness, and an inner circumference. The inner circumference 6A of the female piece 6 is slightly smaller than the outer circumference 4A of the male piece 4 so that the male piece engages the female piece to form a seal to prevent leakage of the contents of the capsule. Optionally, the two pieces may be the same or identical size having means to engage one another, such means being known in the art.

Generally when the two pieces become engaged with one another, a single compartment 10 is formed within the capsule. Referring to FIG. 1, it is known in the art that each capsule piece may also contain a separate smaller compartment 12 (shown as a sub-compartment in male piece 4), in which case a capsule would have a main compartment 10 and a sub-compartment 12 if one of the two piece have a sub-compartment, and a main compartment and two sub-compartments if each of the pieces has a sub-compartment. For example, the sub-compartment may be created by insertion of an inner dividing shell over a desired material, e.g., an emetic or drug. The sub-compartment 12 may be filled with same or different materials as the main compartment 10.

The composition of capsules and capsule pieces are well known in the art. Capsules and capsule pieces typically contain a matrix and a plasticizer.

A matrix is a material that is capable of forming sheets or a film. The matrix may comprise gelatin, cellulose, and cellulose derivatives, carbohydrate polymers, polyvinyl polymers, and other materials known in the art, for example, see U.S. Pat. No. 5,756,123 disclosing a capsule shell comprising hydroxypropylmethyl cellulose, U.S. Pat. No. 6,214,376 disclosing a capsule having a hydrocolloid as a matrix, and U.S. Pat. No. 4,001,211 disclosing thermal gelling cellulose ethers. Preferred matrixes in the present invention are gelatin based.

A plasticizer is a material that increases or decreases the flexibility or toughness of the matrix. Glycerin, sorbitol and other materials known in the art have been used as a plasticizer. For example, see U.S. Pat. No. 5,264,226 disclosing a capsule having a water-soluble cellulose derivative as a matrix, a plasticizer, and a co-plasticizer.

In the present invention, more than one matrix material and more than one plasticizer material may be used to form a capsule.

Other optional ingredients known in the art, such as dyes, flavors, fragrances, surfactants, disintegrants, pH modifiers, and other additives may also be blended therein. Such materials are known in the art.

Methods for manufacturing capsules are well known in the art. For example, pins may be dipped into capsule compositions, and the thickness of the capsules can be varied by varying the temperature of the pins. For example, see U.S. Pat. No. 2,526,683, and U.S. Pat. No. 4,817,367. Additional materials may also be incorporated in to capsule compositions depending on methods of manufacture, including lubricants known in the art.

Tamper resistant capsules and methods of producing tamper resistant capsules are well known in the art. Gelatin locking capsules are known in the art. For example, U.S. Pat. No. 4,040,536 discloses a locking gelatin capsule.

Capsules in the present invention may also be soft gel capsules, i.e., for dosing liquid drugs, and may be filled, i.e., by injection or other means known in the art. The composition of soft gel capsules, methods of manufacturing, and methods of filling are known to those of skill in the art.

As known in the art, a proper amount of the drug is the proper amount or type of drug ingested in accordance with prescribing information and directions, whether by prescription or over the counter. Ingestion of excess drug occurs when drugs are ingested beyond the prescribing information and directions, which may also be an overdose. Overdose occurs when a drug or other chemical is ingested which causes physical damage, injury, illness or death. An overdose for a drug may occur following ingestion of different amount of drugs in different people. For example, person A ingests 10 g of a drug causing an overdose, whereas person B ingesting 10 g of the same drug does not cause an overdose.

Capsules in the present invention are utilized to encapsulate various drugs known in the art that present a danger when abused, or accidentally or purposefully overdosed, for example drugs which may cause death or serious injury to a human at a dosage of less than 50 times the recommended dosage, e.g., less than 20 times or less than 10 times the recommended dosage, including but not limited to acetylsalicylic acid, acetaminophen, vitamins, and medications which are psychotropic, anti-hypertensive, anti-seizure, amphetamine, anti-microbial, antibiotic, anti-viral, anti-retroviral, anti-fungal, anti-depressant, stimulants, anti-histamine, anti-anxiety, tricyclics, tranquilizers, benzodiazepines, hypnotics, mood stabilizers, codeine, selective serotonin reuptake inhibitors, anti-allergy, phenothiazine, chemotherapeutics, amines, monoamine oxidase inhibitors, anti-carcinogens, analgesics, muscle relaxants, ergot preparations, anti-cholinergic, anti-inflammatory, anti-gout preparations, soporfic, hormonal preparations, appetite suppressants, analgesics, muscle relaxants, and opioids.

Liquid formulations of drugs are also known to those in the art. In the present invention, drugs in a liquid formulation may be encapsulated in capsules by methods known to those in the art. In the present invention, drugs in a liquid formulation may also be encapsulated in soft gel capsules by methods known to those in the art.

Emetics and the emetic response caused by such emetics are well known in the art. For example, emetics are disclosed in U.S. Pat. No. 4,269,920. Emetics may broadly be divided into two classes: chemicals that product their effect by acting on the "vomiting centre" in the medulla, and those which act directly on the stomach itself. Certain emetics may also act on the medulla and the stomach, for example, emetine and cephaeline. Representative but non limiting emetics known in the art include methyl cephaeline, cephaeline, emetine hydrochloride, psychotrine, O-methylpsychotrine, emetamine, ipecamine, hydro-ipecamine, ipecacunhun acid, apomorphine, ammonium carbonate, cupric sulfate, tartar emetic, zinc sulfate, blacks mustard, sanguinaria, copper sulfate, eucalyptole, eucalyptus oil, glycynhiza, guaiacol, lobelia, potassium iodide, senega terebene, terpin hydrate, thyme, caffeine, sodium bicarbonate salt, and mixtures thereof.

In the present invention, an emetic is any substance tending to cause gastric contents to be propelled into the mouth, i.e., emesis, or vomit. An emetic dose is the amount of emetic required to be ingested to induce and/or cause emesis. An emetic dose causes some of the gastric contents to be expelled, preferably a majority of gastric contents to be expelled, more preferably substantially all of gastric contents to be expelled.

Preferred emetics include emetics that cause an emetic response when administered orally, and act upon the stomach. Preferred emetics do not produce nausea when a dose smaller than an emetic dose is ingested, but immediately cause emesis when an emetic dose is ingested. Preferred emetics immediately cause emesis when an emetic dose is ingested, i.e., within 1 hour of ingesting an emetic dose, preferably within 45 minutes, more preferably within 30 minutes, still more preferably within 20 minutes of ingesting an emetic dose, or within 15 minutes of consuming an emetic dose. If an overdose of drugs causes a person to lose consciousness, preferably emesis occurs prior to the person losing consciousness to avoid pulmonary aspiration. If a secondary material which blocks the emetic response, i.e., alcohol, is ingested prior to, with, or after ingestion of an emetic dose, emesis preferably occurs prior to impairment of vomiting.

In the present invention, an emetic embedded piece is a piece of a capsule having a matrix, plasticizer, and at least one emetic. An emetic embedded piece may be formed by various methods known in the art. When manufacturing an emetic embedded piece, a predetermined amount of emetic is added to a matrix and plasticizer composition so that the piece can contain a predetermined amount of emetic (expressed in percentage weight, or mass per piece). This admixture of emetic, matrix, and plasticizer is then formed into a male or female capsule piece.

Alternatively, a capsule piece may have a sub-compartment, and an emetic embedded piece can be formed by adding one or more emetics to the sub-compartment. The sub-compartment is subsequently sealed to form an emetic embedded piece. The emetic embedded piece may also be formed from an admixture of matrix, plasticizer, and emetic, in addition to an emetic in the sub-compartment. The emetic in the admixture and the sub-compartment may be the same or different emetics.

In the present invention, an emetic embedded capsule is a capsule having a matrix, plasticizer, and at least one emetic.

Alternatively, an emetic embedded capsule may be formed with one emetic embedded piece and a second capsule piece. The emetic embedded piece and non-emetic embedded piece may consist of different matrix and plasticizer compositions so that the pieces dissolve or rupture in the gastric lumen at different times or different rates.

Alternatively, an emetic embedded capsule is formed with two emetic embedded pieces. The emetic embedded pieces may consist of different matrix and plasticizer compositions from each other so that the pieces dissolve or rupture in the gastric lumen at different rates or different times.

Alternatively, an emetic embedded capsule can be formed when a drug is contained within a sub-compartment of a capsule piece, and an emetic is contained within the main compartment of the capsule.

Alternatively, an emetic embedded capsule can be formed when the drug is contained within a sub-compartment of a capsule piece formed from an admixture of a matrix, plasticizer and emetic, and more emetic is contained within the main compartment of the capsule. The emetic in the admixture may be the same or a different emetic contained within the main compartment.

In the present invention, an emetic embedded piece with one matrix and plasticizer composition may be used with an emetic embedded piece having a different matrix and plasticizer composition. Difference in composition would allow for the capsules to dissolve or rupture in the gastric lumen at different rates or different times.

In the present invention, more than one emetic may be utilized to form an emetic embedded piece. In another embodiment of the present invention, an emetic embedded capsule may be formed with emetic embedded pieces containing different emetics.

In the present invention, it is possible to have emetic embedded capsules to have different colors according to the amount of emetic present. For example, an emetic embedded capsule impregnated with 100 mg of an emetic is black; an emetic embedded capsule impregnated with 200 mg of an emetic is blue; an emetic embedded capsule impregnated with 300 mg of an emetic is red; an emetic embedded capsule impregnated with 400 mg of an emetic is yellow; an emetic embedded capsule impregnated with 500 mg of an emetic is white.

In another embodiment of the present invention, emetic embedded pieces can be of different colors according to the amount of emetic present. For example, an emetic embedded piece impregnated with 50 mg of an emetic is black; an emetic embedded piece impregnated with 100 mg of an emetic is blue; an emetic embedded piece impregnated with 150 mg of an emetic is red; an emetic embedded piece impregnated with 200 mg of an emetic is yellow; an emetic embedded piece impregnated with 250 mg of an emetic is white. Thus an emetic embedded capsule containing 150 mg of an emetic would be a black and a blue emetic embedded piece (50 mg in a black emetic embedded piece, and 100 mg in a blue emetic embedded piece); an emetic embedded capsule containing 300 mg of an emetic would be a black and a white emetic embedded piece (50 mg in a black emetic embedded piece, and 250 mg in a white emetic embedded piece), or two red emetic embedded pieces (150 mg in two red emetic embedded pieces).

In another embodiment of the present invention, emetic embedded pieces and capsules can be different colors depending on the emetic or combination of emetics embedded within the piece or capsule. For example, an emetic embedded piece containing zinc sulfate is green; an emetic embedded piece containing apomorphine is yellow; an emetic embedded piece containing zinc sulfate and apomorphine is red; an emetic embedded capsule formed with an apomorphine embedded piece and a zinc sulfate embedded piece has a yellow and a green emetic embedded piece.

In one embodiment of the present invention, a drug, optionally along with excipients, such as fillers, binders, disintegration agents, lubricants, colorants, or other conventional adjuvants, is packaged into the emetic embedded capsule.

Many drugs known in the art are provided in tablet dosage forms comprising some particulated forms of ingredients. It is known in the art that tablets may also contain excipients, such as fillers, binders, disintegration agents, lubricants, colorants, or other conventional adjuvants.

In one embodiment of the present invention, a tablet is "ground up" along with any excipients in the tablet, such as fillers, binders, disintegration agents, lubricants, colorants, or other conventional adjuvants, and is packaged into the emetic embedded capsule.

The present invention can also be used to encapsulate a tablet, capsule, or soft gel capsule containing one or more drugs and excipients, such that the drug is first contained within a non-emetic embedded capsule or tablet, and then the non-emetic embedded capsule or tablet is encapsulated within an emetic embedded capsule. The matrix and plasticizer selected to form the emetic embedded capsule can be a different composition from the matrix and plasticizer that actually encapsulates the tablet or capsule containing the drugs and excipients so that the differences in composition would allow for the capsules to dissolve or rupture in the gastric lumen at different rates or different times.

In the present invention, the amount of drug administered to a patient can be independent of the amount of the emetic embedded within the capsule. One of ordinary skill in the art can readily determine the amount of drug needed for a particular treatment. One of ordinary skill in the art can also readily determine the amount of a drug a patient can ingest without an overdose. One of ordinary skill in the art can also determine the kind and amount of a particular emetic or combination of emetics a person needs to ingest to induce emesis. Thus, one of ordinary skill can select emetic embedded pieces or capsules to provide to a patient, such that the patient would ingest a sufficient amount of emetic to induce emesis before ingesting, or concurrently ingesting, a sufficient amount of drug to create an overdose.

When orally administered to a patient, the emetic embedded capsule passes to the stomach where the emetic embedded capsule dissolves or ruptures, and the emetic is released into the stomach. If an emetic dose is ingested, emesis should occur before any significant amount of drug is released or absorbed so that the drug is expelled from the body by emesis.

The amount of the emetic in an individual emetic embedded capsule is such that the amount of emetic present will not induce emesis. When an appropriate amount of the drug is ingested, no emetic response is provoked. However, when excess drugs are ingested, emesis occurs.

The present invention is intended to provide flexibility to healthcare professionals, such as doctors and pharmacists, in prescribing and dispensing a wide variety of drugs to individual patients.

In the present invention, the consumption of a number of emetic embedded capsules does not produce nausea or retching. However, consumption of more emetic embedded capsules may cause nausea, retching and emesis. A preferred emetic does not cause nausea or retching prior to ingesting an emetic dose.

An effective amount of emetic to be embedded in an emetic embedded capsule can be calculated by various methods.

In one method, a drug has a specific dosage form and amount (i.e., same drugs have different dosage amounts in tablet or capsule forms). The drug also has a level of overdose or toxicity. It can be readily determined how many tablets or capsules containing a specific amount of drug will need to be ingested before the drug causes an overdose or toxic effect in a person. It can also be readily determined how much emetic is necessary to induce emesis in the same person. A capsule impregnated with a specific mass or amount of emetic is then selected from a group of emetic embedded capsules so that the amount of emetic ingested would cause emesis before a person is able to ingest sufficient quantity of drug to cause overdose, or emesis would occur shortly after the person ingests a sufficient quantity of drug to cause overdose.

For example, a drug is prescribed in 50 mg dosages contained in a tablet or capsule, and causes an overdose at 10 mg/kg. A 70 kg person would thus need to ingest 700 mg, or 14 tablets before an overdose occurs. An emetic induces a response in a person when 5 grams are ingested. Thus, at least 5 grams of emetic would need to be contained in 14 capsules. A pharmacist receives the prescription and recognizes that the person is a suicide risk and chooses to pack the drug into an emetic embedded capsule. The pharmacist has a choice of emetic embedded capsules impregnated with 100 mg, 200 mg, 300 mg, 400 mg, or 500 mg of emetic per capsule. The pharmacist would select a 400 mg emetic embedded capsule, and pack the drug the 400 mg emetic embedded capsule so that if 14 pills are ingested, 5.6 grams of emetic would be ingested to induce emesis in the 70 kg person. Alternatively, a pharmacist could select the 500 mg emetic embedded capsule so that ingestion of 10 of the pills would induce emesis.

In another method, a drug has a specific dosage form and amount (i.e., same drugs have different dosage amounts in tablet or capsule forms). The drug also has a specific level of overdose or toxicity. It can be readily determined how many tablets or capsules containing a specific amount of drug will need to be ingested before the drug causes an overdose or toxic effect in a person. It can also be readily determined how much emetic is necessary to induce emesis in the same person. A capsule impregnated with a type or mixture of emetic is then selected from a group of emetic embedded capsules so that the type or mixture of emetic ingested would cause emesis before a person is able to ingest sufficient quantity of drug to cause overdose, or emesis would occur shortly after the person ingests a sufficient quantity of drug to cause overdose.

For example, a drug is prescribed in 50 mg dosages contained in tablets or capsules, and causes an overdose at 10 mg/kg. A 70 kg person would need to ingest 700 mg, or 14 tablets before an overdose occurs. Thus, an emetic would need to be effective when at least 14 capsules are ingested. A pharmacist receives the prescription and recognizes that the person is a suicide risk, or has small children, or is confused about his dosage, and chooses to pack the drug into an emetic embedded capsule. The pharmacist has a choice of emetic embedded capsules impregnated with different emetics. Three different emetic embedded capsules containing the same mass of emetic are available for encapsulating the drug: a first emetic embedded capsule containing a first emetic that induces a response in a person when 3 grams are ingested; a second emetic embedded capsule containing a second emetic that induces a response in a person when 5 grams are ingested; and a third emetic embedded capsule containing a third emetic that induces a response in a person when 9 grams are ingested. Each emetic embedded capsule only contains 400 mg of the emetic. The drug dispenser would select the first or second emetic embedded capsules so that if 14 pills are ingested, 5.6 grams of the first emetic would be ingested to induce emesis in the 70 kg person, or 5.6 grams of the second emetic would be ingested to induce emesis in the 70 kg person.

In another method, a drug has been prescribed in a unit dose per period of time, e.g., one capsule or tablet once a day, or X number of capsules or tablets per period of time. Consumption of Y tablets or capsules during the same period would result in an overdose of the drug, causing a risk of death or serious harm to the patient. Therefore, an emetic embedded capsule is selected such that the emetic embedded capsule contains enough emetic to induce emesis if a number of capsules approaching the overdose number (Y) capsules were ingested. The appropriate emetic embedded capsule would therefore contain at least 1/Y but less than 1/X of the emetic dose required for an emetic response, or within the range of 1/X to 1/Y.

For example, a drug is prescribed as one tablet at a time. A pharmacist recognizes that an overdose could occur if two tablets are ingested. Accordingly, the pharmacist selects an emetic embedded capsule that contains at least ½ of an emetic dose, but less than 1 emetic dose.

For example, a drug is prescribed as three tablets at a time. A pharmacist recognizes that an overdose would occur if four tablets are ingested. Accordingly, the pharmacist selects an emetic embedded capsule that contains at least ¼ of an emetic dose, but less than ⅓ of an emetic dose.

For example, a drug is prescribed as three tablets at a time. A pharmacist recognizes that an overdose would occur if six tablets are ingested. Accordingly, the pharmacist selects an emetic embedded capsule that contains from at least ⅙ to less than ⅓ of an emetic dose so that if 3 embedded capsules are ingested, emesis does not occur, but if an emetic embedded capsule having ¼ of an emetic dose is selected and 4 or more embedded capsules are ingested, emesis would occur and if an emetic embedded capsule having an ⅕ of an emetic dose is selected and five or more embedded capsules are ingested, emesis would occur, and if an emetic embedded capsule having an ⅙ of an emetic dose is selected and 6 or more embedded capsules are ingested, emesis would occur.

In another method, a drug may contain more than one ingredient that may cause an overdose. The ingredient that is most toxic or potential for overdose should be used in selecting the particular emetic embedded capsule.

In the present invention, it may be convenient for a pharmacist or other health care professional to have one or a series of tables for easy consultation when selecting a particular emetic embedded capsule to encapsulate a drug. The table would identify the emetic, or combination of emetic, and an emetic dosage according to a person's weight, or other characteristic affecting the emetic dosage. Additional tables may also include particular emetics, or combination of emetics, and an emetic dosage according to a person's weight or other characteristic affecting the emetic dosage, and particular drugs.

In another embodiment of the present invention, an emetic composition may be spray coated onto a one or more drugs admixed, or a tablet, capsule, or soft gel containing one or more drugs by any number of methods of spray coating known in the art. The emetic composition contains an emetic and matrix such that when the composition is spray coated onto the drug, tablet, capsule or soft gel. Emetic compositions suitable or spraying have one or more emetics, matrixes, and solvents in which the emetics or matrixes are dissolved or suspended in. After the emetic composition is sprayed onto the capsule, the solvent evaporates, leaving behind the matrix and emetic coated onto the capsule. Solvents are well known in the art, and may include plasticizers and/or organic solvents.

It may be appreciated that certain emetics may be toxic in and of themselves. Although one object of the present invention is to prevent accidental or intentional overdose of drugs, the compositions provided herein should also be safe to ingest on a regular basis, i.e., hourly, four times a day, daily, weekly, in accordance with a doctor's prescription, or in accordance with the proper dosage. Accordingly, all of the forgoing compositions and emetics may also be combined with one or more inert materials known in the art that are substantially inert to a gastrointestinal environment such that when the combination of the emetic chemical and inert material is ingested and passed along the gastrointestinal tract, emesis can be induced when the emetic embedded capsules are ingested in sufficient quantity. However when the emetic embedded capsule is ingested in appropriate quantities, the emetic is not absorbed into the body, but will be passed through the gastrointestinal tract and eliminated from the body. Inert materials suitable to be added to the present invention are known in the art. For example, see U.S. Pat. No. 4,529,583, herein incorporated by reference.

Example 1

Carrageenan is a polysaccharide hydrocolloid which may be extracted from seaweed. Several forms of Carrageenan exist, including the kappa, iota, and lambda forms. Kappa-carregeenan is known to form gels in the presence of potassium cations. Iota-carregeenan is known to form gels in the presence of calcium cations. A carregeen capsule may be prepared by the following steps:

1. Dispersing kappa-carrageenan or a blend of kappa-carrageenan and iota-carrageenan/gelling salt/mannan gum/xanthan gum (if these materials are present) at ambient or at least slightly elevated temperature (higher temperatures, of course, usually being advantageous in the physical dissolution of most materials) in a plasticizer (or mixture of plasticizers);

2. An aqueous solution is prepared by dissolving other additives (e.g., maltodextrin, gum arabic and protein) in water (preferably at about ambient temperature, but some slight elevation or reduction in temperature may be used);

3. The aqueous solution is added to the kappa-carrageenan/plasticizer mixture to form a working composition.

4. The working composition is heated, preferably with stirring to at above 130° F. to below the boiling point of the working mixture, preferably between 135 and 210° P, more preferably between about 160° to 180° F.

5. An emetic is added to the working composition; and

6. The heated working composition containing the emetic can then be transferred or introduced for processing to a conventional gelatin encapsulation machine (films are formed by casting the solution on cooled rotating (e.g., metal such as steel) drums, the films are fed through a series of rollers to counter-rotating dies which form, cut and fill capsules of various sizes.

The following working compositions can be prepared, the ingredients of the compositions being expressed in percentages by weight:

| Composition 1 | |
|---|---|
| Kappa-carrageenan | 4% |
| Maltitol syrup | 30% |
| Sorbitol solution | 2.5% |
| Deionized water | 63.5% |

| Composition 2 | |
|---|---|
| Kappa-carrageenan | 4% |
| Maltitol Syrup | 20% |
| Glycerin | 11% |
| Deionized water | 65% |

An amount of emetic may be added to the working composition so that a capsule piece may be formed containing 0.1 mg to 500 mg of emetic per piece.

Example 2

Acetaminophen is a common prescription and over the counter drug frequently abused, causing an overdose resulting in hepatic toxicity and death. Hepatic toxicity may occur following ingestion of 7.5 grams of acetaminophen, and fatalities may occur following ingestion of 15 grams of acetaminophen. Acetaminophen is available in various dosages, for example, 80, 325, 500, and 650 milligrams per tablet or capsule. Different emetic embedded capsules may be selected to encapsulate the acetaminophen depending on the dosage. For example, ninety four 80 mg acetaminophen tablets would need to be ingested before an overdose would occur; fifteen 500 mg acetaminophen tablets would need to be ingested before an overdose would occur; twelve 650 mg acetaminophen tablets would need to be ingested before an overdose would occur. Accordingly, when encapsulating a 650 mg dose of acetaminophen with an emetic embedded capsule, the emetic embedded capsule should be selected from a group that would induce emesis before twelve capsules are ingested. When encapsulating a 500 mg dose of acetaminophen in an emetic embedded capsule, the emetic embedded capsule should be selected from a group that would induce emesis before fifteen capsules are ingested. When encapsulating a 80 mg dose of acetaminophen with an emetic embedded capsule, the emetic embedded capsule should be selected form a group that would induce emesis before ninety four capsules are ingested.

For example, if acetaminophen is prescribed in 325 mg dosages, an overdose by consumption of the acetaminophen would therefore occur when at least twenty-three 325 mg tablets or capsules are ingested. An emetic embedded capsule embedded with an emetic which causes emesis when 5 grams of emetic is selected to encapsulate the acetaminophen. The emetic embedded capsule would therefore need to contain at least 217 mg of an emetic so that when 7.5 grams of acetaminophen is ingested (23 pills ingested), 5 grams of emetic have also been ingested to induce emesis. Emesis would occur before substantial amount of acetaminophen is released in the stomach and absorbed by the body.

Example 2A

A pharmacy is able to purchase and keep in stock the embodiment shown in FIG. 1, i.e., emetic embedded pieces wherein a predetermined amount of emetic is contained within a capsule piece, and keep a wide variety in stock. A pharmacist has the choice of an emetic embedded piece containing 100 mg, 150 mg, 200 mg, 250 mg, and 300 mg of emetic. When a prescription for a dose of 325 mg of acetaminophen is presented, the pharmacist has the option of selecting emetic embedded pieces having 250 mg, or 300 mg of emetic to encapsulate the acetaminophen. The pharmacist adds the acetaminophen to the emetic embedded piece and seals the capsule with a second capsule piece. Alternatively, the pharmacist can select the 100 mg and 150 mg emetic embedded pieces to encapsulate 325 mg of acetaminophen and form the emetic embedded capsule.

Example 2B

An acetaminophen manufacturer can encapsulate 325 mg acetaminophen dosages within an emetic embedded capsule and market the same under a label "contains emetics."

Example 3

Alprazolam (marketed as XANAX® by Pfizer) is a frequently abused prescription drug and is dispensed in 2 mg tablets. A pharmacist has the option of grinding up the tablet, and encapsulating the powder in an emetic encapsulated capsule, or encapsulating the whole tablet inside of an emetic encapsulated capsule.

Example 4

Fluoxetine hydrochloride (marketed as PROZAC® and SARAFEM® by Eli Lily and Company) is a frequently abused prescription drug and may be prescribed in 10 mg tablets. It is reported that ingestion of 520 mg of fluoxetine hydrochloride has caused death, but there are other side effects that occur much sooner. Due to the toxicity of a low dosage of fluoxetine hydrochloride which may be substantially smaller than a lethal dose, the selected emetic embedded capsule induces emesis with the ingestion of only a few capsules, i.e., ingesting 4, 10, 20, 25, 30, or 40 capsules would induce emesis. Because fluoxetine hydrochloride is a widely prescribed drug, capsule pieces are manufactured with fluoxetine hydrochloride contained within the piece's sub compartment. A pharmacist then creates an emetic embedded capsule by adding an emetic to the capsule piece having the sub-compartment containing fluoxetine hydrochloride, and then sealing the emetic embedded capsule with a non-emetic embedded piece, an emetic embedded piece, or another piece having fluoxetine hydrochloride contained within a sub-compartment.

Example 5

Diazepam (marketed as VALIUM by Roche Pharmaceuticals) is a benzodiazepine derivative which is frequently abused. Oral LD 50 of diazepam is 720 mg/kg in mice, and 1240 mg/kg in rats. Depending on severity of the condition, VALIUM may be prescribed 10 mg 4 times per day. VALIUM is dispensed in 2 mg, 5 mg, and 10 mg tablets. A pharmacist recognizes that the patient has a history of drug abuse, and chooses to pack the diazepam in an emetic encapsulated capsule. The pharmacist also recognizes that the patient is prone to tampering with capsules, so selects an emetic embedded capsule with a tamper resistant lock.

Example 6

Hydrocodone bitartrate (marketed as VICODIN®, VICODIN ES®, and VICODIN HP® by Abbott Laboratories) is a frequently abused opioid analgesic and antitussive. Hydrocodone bitartrate is frequently administered with acetaminophen (i.e., VICODIN® contains 5 mg hydrocodone bitartrate and 500 mg acetaminophen per tablet; VICODIN ES® contains 7.5 mg hydrocodone bitartrate and 750 mg acetaminophen per tablet; and VICODIN HP® contains 10 mg hydrocodone bitartrate and 660 mg acetaminophen per tablet). Hydrocodone bitartrate and acetaminophen can cause toxicity or death. Patients are frequently counseled not to take a double dosage of VICODIN due to the toxicity of hydrocodone bitartrate. A health care professional would therefore be more concerned with the hydrocodone bitartrate because it would cause the toxicity or death rather than the acetaminophen.

Zinc sulfate heptahydrate causes emesis when 0.6 grams are ingested. An emetic embedded capsule should contain between 0.3 and 0.6 grams of zinc sulfate so that when a double dose of VICODIN is ingested, emesis occurs.

Example 7

Triazolm (marketed as HALCION® by Pharmacia & Upjohn) is a hypotonic agent which is abused. Manifestations of overdose may occur after ingestion of 2 mg. HALCION® is dispensed as 0.125 mg and 0.25 mg tablets. Because of the potency of the triazolm and the ability of an individual to ingest more than 4 pills at a time (four 0.25 mg tablets is 2 mg of Triazolm, which could produce an overdose), an emetic embedded capsule should contain sufficient emetic to induce emesis as soon as more than 2 emetic embedded capsules are ingested. Thus, an emetic embedded capsule containing between 0.3 and 0.6 grams of zinc sulfate is used to encapsulate triazolm so that consumption of 1 capsule will not cause emesis, but consumption of 2 capsules will cause emesis.

Example 8

Methylphenidate hydrochloride (marketed as CONCERTA® by McNiel Consumer Healthcare) is a central nervous system stimulant that is frequently abused. CONCERTA® tablets uses osmotic pressure to deliver methylphenidate hydrochloride at a controlled rate. The CONCERTA® tablet resembles a conventional tablet, comprising an osmotically active trilayer core surrounded by a semipermeable membrane with an immediate-release drug overcoat. The trilayer is composed of two drug layers containing the drug and excipients, and a push layer containing osmotically active components. There is a precision laser drilled orifice on the drug layer end of the tablet. Following ingestion, the drug overcoat dissolves, providing an initial dose or methylphenidate. Water permeates through the membrane into the tablet core, and as osmotically active polymer excipients expand, methylphenidate is released through the orifice. The CONCERTA tablet contains biologically inert components which remain intact during gastrointestinal transit and are eliminate in the stool, along with insoluble core components. Accordingly, a CONCERTA® tablet cannot be ground up and encapsulated within an emetic embedded capsule. However, a pharmacist is able to select emetic embedded capsules having a sub-compartment containing an emetic (as shown in FIG. 1), and encapsulating the CONCERTA® tablet to create an emetic embedded capsule containing an appropriate amount of emetic.

Alternatively, manufacturers of CONCERTA® can elect to encapsulate CONCERTA® within the sub-compartment of a capsule piece so that a pharmacist will be able to encapsulate an appropriate amount of emetic in the capsule's main compartment. This allows the pharmacist the flexibility to create custom emetic doses for individuals. An appropriate amount of emetic is a specific mass that would not cause emesis when the drug is ingested in proper quantities, and the number of emetic embedded capsules ingested to induce emesis is less than the number of emetic embedded capsules ingested to cause a drug overdose.

Example 9

Bupropion hydrochloride (marketed as WELLBUTRIN®, and ZYBAN® by GlaxoSmithKline) is an antidepressant frequently abused. WELLBUTRIN® is dispensed as 75 mg or 100 mg tablets, and ZYBAN® is dispensed as 150 mg tablets. In populations of individuals experienced with drugs of abuse, a single dose of 400 mg of WELLBUTRIN produced mild amphetamine-like activity. Bupropion is associated with seizures in approximately 0.4% of patients treated at doses up to 450 mg/day, which may exceed that of other marketed antidepressants by as much as fourfold. The estimated seizure incidence for WELLBUTRIN increases almost 10-fold between 450 mg/day and 600 mg/day. It is recommended that to reduce the risk of seizure, a single dose of WELLBUTRIN or ZYBAN not exceed 150 mg. A pharmacist thus packets ZYBAN into an emetic embedded capsule or emetic embedded piece which would cause emesis when two 150 mg doses are consumed to avoid amphetamine-like activity and reduce the risk of seizure. A pharmacist may also packet 100 mg WELLBUTRIN tablets in an emetic embedded capsule which would cause emesis when 4 tablets are consumed to reduce the risk of seizure, however, will not cause emesis when 2 tablets are consumed which may cause amphetamine-like activity.

The matters set here are offered by way of illustration only and not as limitations. While particular embodiments have been shown and described, it will be apparent to those skilled in the art that changes and modifications may be made without departing from the broader aspects of invention. The actual scope of the protection sought is intended to be defined in the following claims when viewed in their proper perspective based on the prior art.

I claim:

1. A hard capsule piece for encapsulating a drug, wherein the hard capsule piece comprises:
   an emetic;
   a matrix; and
   a plasticizer; and
wherein said emetic is embedded in the hard capsule piece.

2. The hard capsule piece of claim 1, further comprising an inert material.

3. The hard capsule piece of claim 1, wherein said matrix and said plasticizer form a shell having a discrete compartment, said emetic being contained within the compartment, said shell capable of engaging a second capsule piece.

4. The hard capsule piece of claim 1 formed from an admixture of the matrix, the plasticizer, and the emetic.

5. The hard capsule according to claim 1, wherein the capsule comprises a first capsule piece and a second capsule piece cooperatively engaging for encapsulating a drug.

6. The hard capsule of claim 5, which encapsulates a unit dosage of a drug, wherein the weight of the emetic is in the range of 1/X to 1/Y of an emetic dose to induce emesis, with X being the number of unit dosages of the drug prescribed for administration within a particular time period and Y being the number of unit dosages of the drug which would constitute an overdose if taken in the same time period.

7. The hard capsule of claim 5 wherein the emetic is selected from the group consisting of central emetics and gastric emetics.

8. The hard capsule of claim 5 wherein the emetic is selected from the group consisting of emetine, methyl cephaeline, cephaeline, emetine hydrochloride, psychotrine, O-methylpsychotrine, emetamine, ipecamine, hydro-ipecamine, ipecacunhun acid, apomorphine, ammonium carbonate, cupric sulfate, tartar emetic, zinc sulfate, blacks mustard, sanguinaria, copper sulfate, eucalyptole, eucalyptus oil, glycynhiza, guaiacol, lobelia, potassium iodide, senega terebene, terpin hydrate, thyme, caffeine, lobelia inflata, and sodium bicarbonate salt, and combinations thereof.

9. A hard capsule according to claim 5, wherein the hard capsule piece further comprises a drug, and wherein the amount of emetic and the amount of the drug is such that the number of capsules needed to be ingested to cause emesis is fewer than the number of capsules needed to be ingested to cause overdose of said drug.

10. The hard capsule piece according to claim 9 wherein the drug is a drug which can cause death or serious injury to a human at a level of 50 or fewer times the recommended dosage.

11. The hard capsule piece of claim 9 wherein the drug is selected from the group consisting of acetylsalicylic acid, acetaminophen, vitamins, psychotropics, anti-hypertensive, anti-seizures, amphetamines, anti-microbials, antibiotics, anti-virals, anti-retrovirals, anti-fungals, anti-depressants, stimulants, anti-histamines, anti-anxiety, tranquilizers, benzodiazepines, hypnotics, mood stabilizers, codeine, selective serotonin reuptake inhibitors, anti-allergy, phenothiazine, chemotherapeutics, amines, monoamine oxidase inhibitors, anti-carcinogens, analgesics, muscle relaxants, ergot preparations, anti-cholinergic, anti-inflammatory, anti-gout preparations, soporfic, hormonal preparations, appetite suppressants, analgesics, muscle relaxants, and opioids, and combinations thereof.

12. The hard capsule piece according to claim 11 wherein the drug is codeine.

13. The hard capsule piece according to claim 11 wherein the drug is an anti-depressant.

14. The hard capsule piece according to claim 11 wherein the drug is an opioid.

15. The hard capsule piece according to claim 11 wherein the drug is an analgesic.

16. The hard capsule piece according to claim 11 wherein the drug is an antipsychotic.

17. The hard capsule piece according to claim 9 wherein the emetic is any substance capable of inducing emesis.

18. The hard capsule piece according to claim 17 wherein the emetic is selected from the group consisting of emetine, methyl cephaeline, cephaeline, emetine hydrochloride, psychotrine, O-methylpsychotrine, emetamine, ipecamine, hydro-ipecamine, ipecacunhun acid, apomorphine, ammonium carbonate, cupric sulfate, tartar emetic, zinc sulfate, blacks mustard, sanguinaria, copper sulfate, eucalyptole, eucalyptus oil, glycynhiza, guaiacol, lobelia, potassium iodide, senega terebene, terpin hydrate, thyme, caffeine, and sodium bicarbonate salt, and combinations thereof.

19. A method of preventing or reducing the risk of a drug overdose comprising encapsulating a drug in the hard capsule according to claim 5 such that ingesting of a proper amount of drug does not induce emesis, but ingestion of excess drug induces emesis.

20. A method of preventing or reducing the risk of overdose of a drug administered to a patient considered to be at risk of accidentally or deliberately taking an overdose of the drug, comprising encapsulating the drug in the hard capsule according to claim 5 such that ingesting of a proper amount of the drug does not induce emesis, but ingestion of excess drug induces emesis.

21. The hard capsule piece according to claim 3, wherein the capsule comprises a first capsule piece and a second capsule piece cooperatively engaging for encapsulating a drug.

22. The hard capsule piece according to claim 4, wherein the capsule comprises a first capsule piece and a second capsule piece cooperatively engaging for encapsulating a drug.

* * * * *